United States Patent [19]

Determann et al.

[11] 4,118,279

[45] Oct. 3, 1978

[54] STABILIZING AGENT FOR ENZYMES

[75] Inventors: Helmut Determann, Starnberg; Erich Bernt, Munich; Werner Dollacker, Weilheim, all of Germany; Ingeborg Gutman, deceased, late of Bad Heilbrunn, Germany, by Siegfried Gutmann, administrator; by Gudrun Engelhardt, administrator, Saarbruecken, Germany

[73] Assignee: Boehringer Mannheim GmbH, Mannheim-Waldhof, Germany

[21] Appl. No.: 843,298

[22] Filed: Oct. 18, 1977

[30] Foreign Application Priority Data

Oct. 27, 1976 [DE] Fed. Rep. of Germany ....... 2648759

[51] Int. Cl.² .............................................. C07G 7/02
[52] U.S. Cl. ..................................... 195/63; 195/103.5 R
[58] Field of Search ....................... 195/63, 68; 424/94

[56] References Cited
PUBLICATIONS

Chemical Abstracts, vol. 81, 23606p (1974).

*Primary Examiner*—Lionel M. Shapiro
*Attorney, Agent, or Firm*—Burgess, Dinklage & Sprung

[57] ABSTRACT

Enzyme preparations, particularly enzyme preparations containing organic sulfhydryl compounds for activation, are stabilized by means of a stabilizing agent comprising oxypolygelatine, especially oxypolygelatine having an average molecular weight of from 10,000 to 50,000.

4 Claims, No Drawings

STABILIZING AGENT FOR ENZYMES

The present invention is concerned with stabilized enzyme preparations. More specifically, the invention is concerned with stabilized enzyme compositions which require organic sulfhydryl compounds for activation.

It is known that enzyme preparations, for example, enzyme-containing reagents for clinical or foodstuff analysis, standarized test preparations, soluble enzyme preparations for catalytic, preparative purposes and the like, must be stabilized to prevent a loss of enzymatic activity. Enzymatically-inactive protein preparations have proved to be especially useful as stabilizing agents for this purpose. In particular, albumins, such as bovine serum albumin, are, for this reason, frequently added to such enzyme-containing preparations as stabilizing agents and as protective colloids for the enzymes.

However, stabilizing agents based on proteins are sensitive to denaturing and can lead to the formation of highly undesirable turbidities which are especially troublesome when optical measurements are to be carried out on solutions containing the enzyme. This is, for example, regularly the case in analytical compositions in which the measurement reaction is to be monitored photometrically, nephelometrically or by other optical methods.

This difficulty occurs especially when the enzyme preparation to be stabilized contains organic sulfhydryl compounds, such sulfhydryl compounds (SH compounds) being needed by many enzymes for activation. Furthermore, such SH compounds are frequently added to combined preparations as stabilizers and especially as oxidation protection agents, not only for some enzymes, but also for non-proteinaceous substances which are sensitive to oxidation. However, such SH compounds frequently lead to a denaturing of the enzymatically-inactive proteins, for example, serum albumin, added as stabilizing agents. This denaturing then leads to the appearance of the above-described turbidities.

The present invention provides stabilized enzyme preparations which comprise a stabilizing agent for enzymes, the stabilizing effectiveness of which is equal to that of the previously used stabilizers based on natural proteins, but which, under the conditions appearing in the case of enzymatic preparations, shows no tendency towards the formation of turbidities. Furthermore, the stabilizing agent used is stable toward SH compounds and does not give rise to precipitations.

The enzyme preparation according to the present invention contains, as a stabilizing agent, oxypolygelatine (OPG).

Oxpolygelatine is known and is commercially available. It can be obtained by the hydrolytic decomposition of gelatine, reaction of the decomposition products with glyoxal and oxidation of the reaction product with an oxidation agent, such as hydrogen peroxide. The average molecular weight of the oxypolygelatine used according to the present invention is preferably from 10,000 to 50,000.

For use according to the present invention, the oxypolygelatine should be free of salts and other low molecular weight components. Therefore, the oxypolygelatine used according to the present invention as a stabilizing agent is preferably one which has been freed from low molecular weight components by dialysis, followed by lyophilization.

The stabilizing agent used according to the present invention can consist of oxypolygelatine alone, but can also contain one or more known stabilizing agents, i.e., can be a component of a complex stabilizing agent. Its stabilizing effectiveness corresponds at least to that of the previously used stabilizing agents based on native proteins. This relates to a weight basis, i.e., for the achievement of an equal stabilizing effect, the oxypolygelatine is used in the same amount by weight as the native, stabilizing proteins, such as serum albumin. Therefore, in existing enzyme-containing preparations which have hitherto been stabilized by native proteins, the latter can be replaced by an equal amount by weight of oxypolygelatine in order to achieve the advantages of the present invention.

The stabilizing agent used according to the present invention can be used not only for stabilizing enzymes activated by SH compounds, but also for other enzymes. Examples of enzymes which can be present in the stabilized enzyme preprations according to the present invention include hexokinase (HK), glucose-6-phosphate dehydrogenase (G6P-DH), creatine kinase (CK), lactate dehydrogenase, malate dehydrogenase, glutamate dehydrogenase, alcohol dehydrogenase, aldolase, triose isomerase and diaphorase.

Typical SH compounds used for activation or oxidation inhibition include the following:
derivatives of cysteine and homocysteine:
N-guanyl-L-cysteine
N-guanyl-DL-isocysteine
N-acetyl-S-guanyl-L-cysteine
N-acetyl-S-benzyl-L-cysteine
N,S-diguanyl-L-cysteine
S-carbamoyl-L-cysteine
S-carboxymethyl-L-cysteine
S-guanyl-L-cysteinehydantoin
S-acetylguanyl-DL-cysteineazolactone
2-imino-L-cysteinehydantoin
N-acetyl-DL-homocysteinethiolactone
DL-homocysteinethiolactone
L-cysteine
L-cysteine methyl ester
L-cysteine ethyl ester
N-acetyl-L-cysteine
N-acetyl-DL-isocysteine
HS-containing peptide (tripeptide):
reduced glutathione
thioalcohols, including mercaptans:
1,3-dimercaptopropan-2ol
2,3-dimercaptopropanol
1,2-dimercaptoethane
dithiothreitol
dithioerythritol
mercaptoethanol
thio acids:
thioglycolic acid
L-thiazolidine-4-carboxylic acid
as well as aminoethylisothiouronium bromide.

The following Example is given for the purpose of illustrating the present invention:

EXAMPLE

A reagent solution of the following Composition A was filled in 1.00 ml. amounts into ampoules and the solution lyophilized. The lyophilizate was stored for 3 weeks at +33° C. After this time, for the determination of the stability of the hexokinase (HK) and glucose-6-phosphate dehydrogenase (G6P-DH), of the function (verification of the creatine kinase (CK) activity in the control serum), as well as of the turbidity, the lyophilizate was dissolved in 2.5 ml. amounts of a buffer solution of Composition B and the appropriate tests then carried out.

Reagent solution of Composition A:

220 mg. adenosine diphosphoric acid 653 mg. disodium adenosine monophosphate 445 mg. disodium nicotinamide-adenine-dinucleotide phosphate 2887 mg. disodium creatine phosphate hexahydrate 8.5 mg. N-acetylcysteine 880 U hexokinase 450 U glucose-6-phosphate dehydrogenase without additive or with 2.0 mg. dialy ed and lyophilized oxpolygelatine or with 2.0 mg. bovine serum albumin.

These substances were dissolved in 100 ml. water and the solution obtained was filled in 1.0 ml. amounts into ampoules and lyophilized.

Buffer solution of Composition B:

496 mg. imidazole 288 mg. glucose monohydrate 156 mg. magnesium acetate tetrahydrate 82 mg. ethylenediamine-tetraacetic acid add acetic acid to give a pH value of 6.7 and add double distilled water to give 70 ml.

The results of the tests carried out are summarized in the following three Tables:

1. Measurement of activity of hexokinase and G6P-DH (in U/flask).

| | without stabilization agent | | with OPG | | with albumin | |
|---|---|---|---|---|---|---|
| | HK | G6P-DH | HK | G6P-DH | HK | G6P-DH |
| initial value before lyophilization | 8.9 | 4.4 | 8.9 | 4.5 | 8.8 | 4.5 |
| after 3 weeks/33° C. | 0.1 | 0.05 | 6.9 | 4.0 | 6.7 | 4.2 |

2. Verification of the CK activity in control serum (in % of nominal value).

| | without stabilization agent | with OPG | with albumin |
|---|---|---|---|
| Initial value before lyophilization | 97% | 99% | 97% |
| after 3 weeks/33° C. | 5% | 96% | 95% |

3. Measurement of turbidity of dissolved lyophilizate at 546 nm.

| | without stabilization agent | with OPG | with albumin |
|---|---|---|---|
| initial value before lyophilization | 0.125 | 0.135 | 0.330 |
| after 3 weeks/33° C. | 0.128 | 0.138 | 1.235 |

The above-given comparative experimental values show that, without the addition of a stabilizing agent, a very rapid inactivation of the enzymes takes place. With the addition of the known stabilizing agent serum albumin, the enzymes can admittedly be well stabilized but a strong turbidity results due to denaturing of the stabilizing agent which, in the optical test, brings about a very high initial extinction. Because of this high initial extinction, exact values can no longer be measured with conventional photometers.

On the other hand, in the case of adding the stabilizing agent used according to the present invention, not only is the maintenance of activity very good even in the case of accelerated ageing at an elevated temperature, but also there is a complete absence of turbidity due to the stabilizing agent.

It will be understood that the specification and examples are illustrative but not limitative of the present invention and that other embodiments within the spirit and scope of the invention will suggest themselves to those skilled in the art.

What is claimed is:

1. An enzyme preparation containing oxypolygelatine as a stabilizing agent.

2. An enzyme preparation as claimed in claim 1 wherein said oxypolygelatine has been freed from salts and low molecular weight components by dialysis and lyophilization.

3. An enzyme preparation according to claim 1 wherein said oxypolygelatine has an average molecular weight of from 10,000 to 50,000.

4. Enzyme preparation as claimed in claim 1 also containing a sulfhydryl compound for the activation of an enzyme of said enzyme preparation.

* * * * *